(12) United States Patent
Griffith et al.

(10) Patent No.: US 9,277,845 B2
(45) Date of Patent: Mar. 8, 2016

(54) FLEXIBLE CREVICE TOOL FOR VACUUM CLEANERS

(75) Inventors: Aaron P. Griffith, Grand Rapids, MI (US); Joseph A. Fester, Ada, MI (US); Jonathan L. Miner, Rockford, MI (US)

(73) Assignee: BISSELL Homecare, Inc., Grand Rapids, MI (US)

( * ) Notice: Subject to any disclaimer, the term of this patent is extended or adjusted under 35 U.S.C. 154(b) by 1587 days.

(21) Appl. No.: 11/684,224

(22) Filed: Mar. 9, 2007

(65) Prior Publication Data

US 2007/0209154 A1    Sep. 13, 2007

Related U.S. Application Data

(60) Provisional application No. 60/743,454, filed on Mar. 10, 2006.

(51) Int. Cl.

| | |
|---|---|
| *A47L 7/04* | (2006.01) |
| *A47L 5/30* | (2006.01) |
| *A47L 5/32* | (2006.01) |
| *A47L 5/34* | (2006.01) |
| *A47L 9/00* | (2006.01) |
| *A47L 9/02* | (2006.01) |
| *A47L 9/04* | (2006.01) |
| *A47L 9/12* | (2006.01) |
| *A47L 9/16* | (2006.01) |
| *A47L 9/24* | (2006.01) |
| *A47L 9/32* | (2006.01) |
| *A61L 9/00* | (2006.01) |
| *A61L 9/20* | (2006.01) |

(52) U.S. Cl.
CPC ... *A47L 7/04* (2013.01); *A47L 5/30* (2013.01); *A47L 5/32* (2013.01); *A47L 5/34* (2013.01); *A47L 9/00* (2013.01); *A47L 9/02* (2013.01); *A47L 9/04* (2013.01); *A47L 9/122* (2013.01); *A47L 9/1625* (2013.01); *A47L 9/1641* (2013.01); *A47L 9/1683* (2013.01); *A47L 9/1691* (2013.01); *A47L 9/24* (2013.01); *A47L 9/244* (2013.01); *A47L 9/325* (2013.01); *A61L 9/00* (2013.01); *A61L 9/20* (2013.01)

(58) Field of Classification Search
CPC ............... A47L 9/02; A47L 9/04; A47L 9/00; A47L 7/04; A47L 5/30; A47L 5/32; A47L 9/122; A47L 9/1625; A47L 9/1641; A47L 9/1683; A47L 9/1691; A47L 9/24; A47L 9/244; A47L 9/325
USPC ...................... 15/415.1, 414, 417, 420, 300.1
See application file for complete search history.

(56) References Cited

U.S. PATENT DOCUMENTS

| 3,189,053 | A | * | 6/1965 | Parr .............................. 138/133 |
| 4,114,230 | A | * | 9/1978 | MacFarland .................... 15/330 |
| D307,174 | S | * | 4/1990 | Bjorkman et al. ........... D23/266 |

(Continued)

FOREIGN PATENT DOCUMENTS

GB    2223934 A    4/1990

*Primary Examiner* — Robert Scruggs
(74) *Attorney, Agent, or Firm* — McGarry Bair PC

(57) ABSTRACT

An accessory tool for a vacuum cleaner comprises an elongated body having a plurality of furrows for imparting flexibility to the accessory tool. The elongated body is further be made of a material that is selected to impart flexibility to the accessory tool so that the longitudinal axis of the elongated portion can be bent about a radius through an angle up to 45° without kinking or breaking in a direction transverse to and laterally of elongated cross-sectional configuration.

17 Claims, 4 Drawing Sheets

(56) References Cited

U.S. PATENT DOCUMENTS

| | | | |
|---|---|---|---|
| 5,109,568 A * | 5/1992 | Rohn et al. | 15/410 |
| 5,452,493 A | 9/1995 | Galindo | |
| 6,345,407 B1 * | 2/2002 | Jupp | 15/323 |
| 7,036,184 B2 | 5/2006 | Kim | |
| 7,188,387 B2 * | 3/2007 | Dicioccio | 15/321 |
| 7,418,763 B2 * | 9/2008 | Shaver et al. | 15/330 |
| 2002/0170140 A1 * | 11/2002 | Diaz et al. | 15/415.1 |
| 2003/0163891 A1 * | 9/2003 | Nagai et al. | 15/414 |
| 2005/0183228 A1 * | 8/2005 | Snyder | 15/314 |
| 2007/0017060 A1 * | 1/2007 | Zimmerle et al. | 15/315 |

* cited by examiner

FLEXIBLE CREVICE TOOL FOR VACUUM CLEANERS

CROSS REFERENCE TO RELATED APPLICATIONS

This application claims priority to U.S. provisional patent application Ser. No. 60/743,454, filed Mar. 10, 2006, which is incorporated herein by reference in its entirety.

BACKGROUND OF THE INVENTION

1. Field of the Invention

This invention relates to above-the-floor cleaning attachments for vacuum cleaners. In one of its aspects, the invention relates to a cleaning tool that is adaptable for different types small constricted areas.

2. Description of the Related Art

In addition to having floor suction nozzles for on-the-floor cleaning, vacuum cleaners commonly have cleaning attachment tools that used for above-the floor cleaning operations, where the attachment tool is connected to a vacuum hose on a vacuum cleaner. When performing above-the-floor cleaning, surfaces to be cleaned in small, narrow and/or constricted areas are notoriously difficult to clean because many attachment tools are too large to fit into these areas. Crevice tools specifically developed for cleaning surfaces in small, narrow and/or constricted areas often fail as well since crevice tools are traditionally long, straight, and stiff, and cannot be fit into curved spaces very easily. More over, these crevice tools often require a user to bend over or stoop to achieve a proper orientation between the crevice tool and the surface to be cleaned, which can be painful to many users.

SUMMARY OF THE INVENTION

According to the invention, an accessory tool for a vacuum cleaner comprises a body having an attachment end for attachment to a suction hose and an elongated portion having a nozzle opening for ingestion of debris-containing air and a plurality of spaced furrows formed transverse to a longitudinal axis of the body, whereby the furrows are shaped and the elongated portion is made of a material that is selected to impart flexibility to the elongated portion transversely to the longitudinal axis.

In one embodiment, the furrows can be circumferentially formed around the elongated portion. The nozzle opening can comprise a rim that lies in a plane at an acute angle to the longitudinal axis of the body. The furrows can lie in planes that are parallel to the plane of the rim.

In another embodiment, the body can be integrally molded in one piece. The elongated portion can have an elongated cross-sectional configuration perpendicular to the longitudinal axis of the body. The elongated portion can be oval in cross-sectional configuration. The elongated portion can taper toward the nozzle opening.

In yet another embodiment, at least the elongated portion can be made of one of nitrile rubber, thermoplastic urethane, polypropylene, and polyurethane. The longitudinal axis of the elongated portion can be bent about a radius up to 45° without kinking or breaking. In a preferred embodiment, the longitudinal axis of the elongated portion can be bent about a radius up to 90° without kinking or breaking.

Further according to the invention, an accessory tool for a vacuum cleaner comprises a body having an attachment end for attachment to a suction hose and an elongated portion that has an elongated cross-sectional configuration perpendicular to a longitudinal axis and has a nozzle opening for ingestion of debris-containing air wherein the elongated portion is made of a material and is so designed to impart flexibility to the elongated portion transversely to the longitudinal axis so that the longitudinal axis of the elongated portion can be bent about a radius through an angle up to 45° without kinking or breaking.

In one embodiment, the longitudinal axis of the elongated portion can be bent about a radius through an angle up to 45° without kinking or breaking in a direction transverse to and laterally of elongated cross-sectional configuration.

In another embodiment, a wire is affixed to or within the elongated portion, wherein the wire has sufficiently stiffness and malleability so that the elongated portion can be formed to and can releasably remain in bent position.

DESCRIPTION OF THE PREFERRED EMBODIMENT

Figure 1:
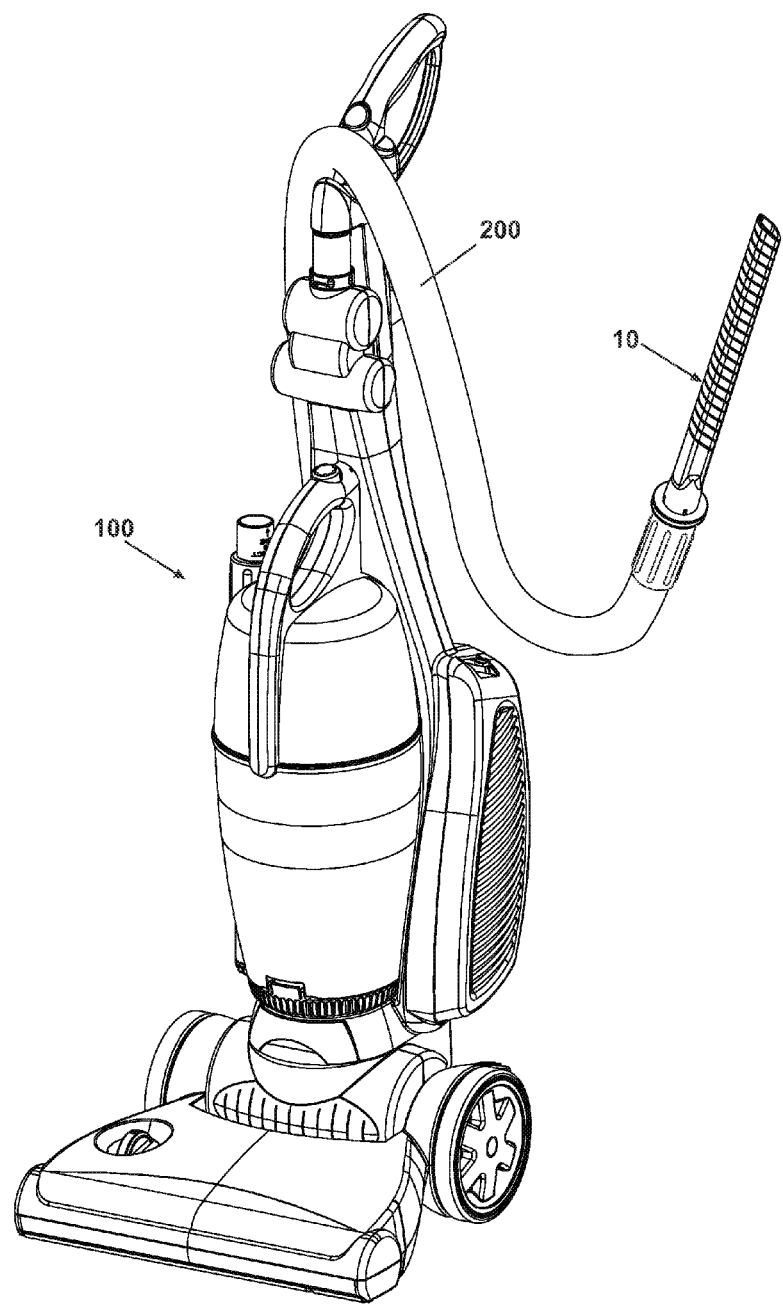
FIG. 1 is a perspective view of a flexible crevice tool according to the present invention coupled with a vacuum cleaner.

Referring to the drawings, and in particular to FIG. 1, a cleaning attachment tool for a vacuum cleaner 100 is provided. The cleaning attachment tool comprises a flexible crevice tool 10 that can be coupled with a vacuum hose 200 connected to the vacuum cleaner 100 for above-the-floor vacuum cleaning. The crevice tool 10 can be used with any type of vacuum cleaner, including, but not limited to, upright vacuum cleaners (illustrated), canister vacuum cleaners, stick-type vacuum cleaners, hand-held vacuum cleaners, etc.

Figure 2:
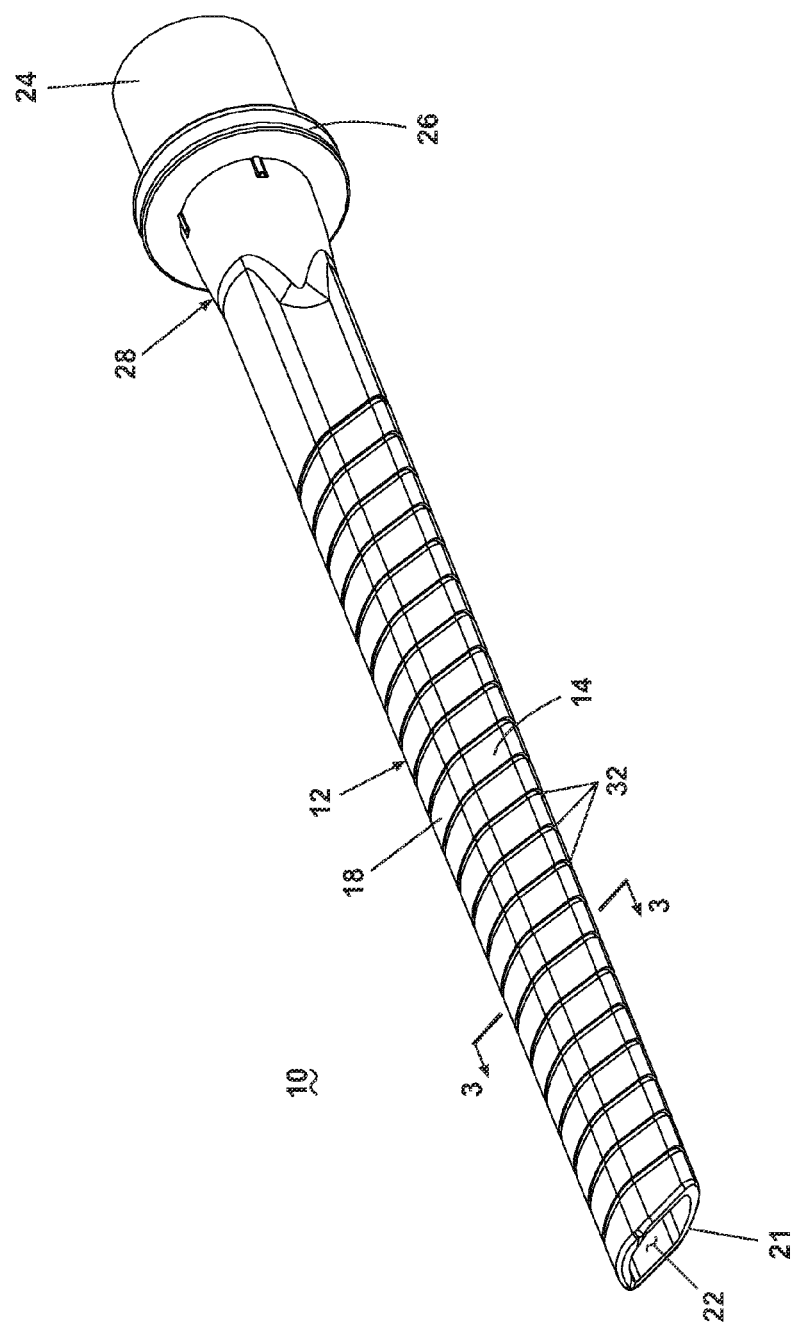
FIG. 2 is a perspective view of the flexible crevice tool from FIG. 1.
Figure 3:
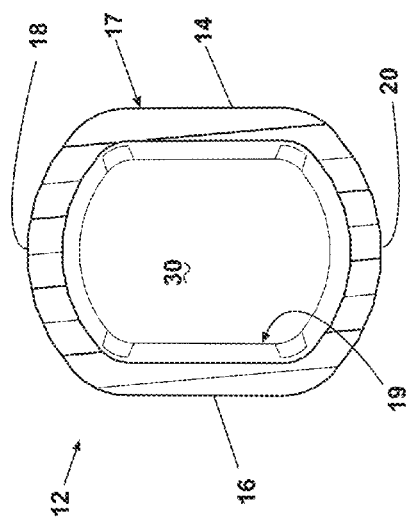
FIG. 3 is a cross-sectional view taken through line 3-3 of FIG. 2.
Figure 4:
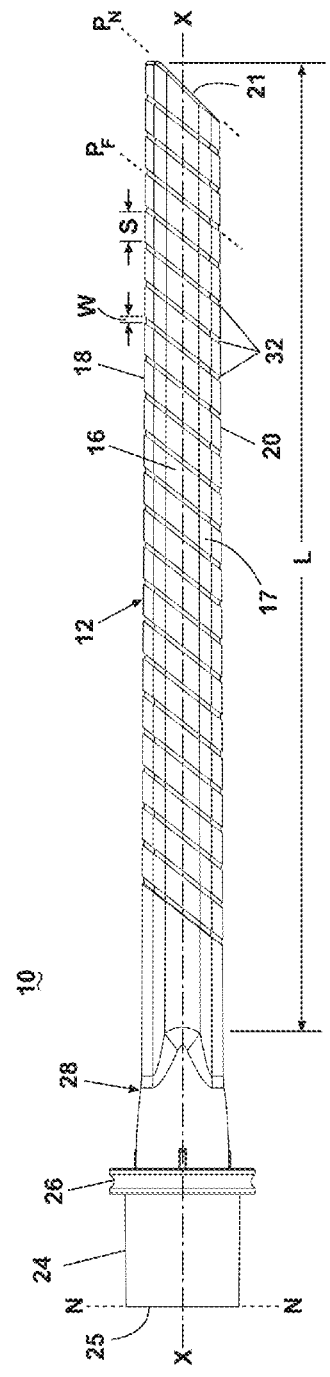
FIG. 4 is a side view the flexible crevice tool from FIG. 1.

Referring to FIGS. 2-4, the flexible crevice tool 10 comprises an elongated hollow body comprising an elongated portion 12 that is made of a flexible material that allows the crevice tool 10 to bend or deform as needed, without kinking, so that when a user is cleaning a surface in a hard-to-reach area, for example underneath or behind furniture. The crevice tool 10 can further be flexed to a wide range of curved configurations which requires the user to bend over or stoop less often to achieve a desired cleaning orientation between the crevice tool 10 and the surface to be cleaned. The material has sufficient resilience to otherwise retain a relatively straight shape. The flexible material preferably has a durometer in the range of 75-90 Shore A. Some non-limiting examples of flexible materials that can be used to construct the elongated portion 12 include nitrile rubber, thermoplastic urethane, polypropylene, and polyurethane.

As illustrated, the elongated portion 12 has a length L and includes a pair of spaced, generally straight side walls 14, 16 joined by a curved upper wall 18 and a curved lower wall 20. The elongated portion 12 has an elongated cross-sectional configuration, whereby the distance between the upper wall 18 and the lower wall 20 is greater than the distance between the side walls 14, 16. As illustrated, the cross-sectional configuration is roughly oval, although other cross-sectional configurations are possible. The walls 14, 16, 18, 20 define an exterior surface 17 and an interior surface 19 of the elongated portion 12. The interior surface 19 can be substantially smooth. The elongated portion 12 has a nozzle rim 21 at one end defining a nozzle opening 22 through which air containing dirt and debris is ingested. The nozzle rim 21 can be formed so that it lies in a plane $P_N$ that is at an acute angle to a longitudinal axis X of the crevice tool 10, such that a user can hold the crevice tool 10 in an ergonomic manner while maintaining the nozzle opening 22 relatively flat against a surface being cleaned.

An attachment end 24 is positioned opposite the nozzle opening 22 and is sized to couple with a vacuum hose, such as the vacuum hose 200, by a friction fit. As best seen in FIG. 4, the attachment end 24 has a rim 25 defining an opening (not shown) that extends along a normal axis N of the crevice tool 10. It is noted that the circumferential flange 26 on the attachment end 24 provides a stop for the end of the vacuum hose 200. The attachment end 24 can be continuously molded with the elongated portion 12. Alternately, the attachment end 24 can be made of a stiffer material than the elongated portion 12 to prevent flexing at the junction between the crevice tool and the vacuum hose, and can be attached to the elongated portion 12 using any suitable means. The material chosen for the elongated portion 12 preferably has suitable tear strength to withstand repeated flexing of the elongated portion 12 without separating from the attachment end 24.

As illustrated, the attachment end 24 has a roughly circular cross-sectional configuration. Since the preferred cross-sectional configuration of the elongated portion 12 is oval, a transition portion 28 is formed between the elongated portion 12 and the attachment end 24, where the cross-sectional configuration of the crevice tool 10 changes from oval to circular. The length L of the elongated portion 12 can be defined between the nozzle rim 21 and the transition portion 28.

An air flow channel 30 is defined by the interior surface 19 through the crevice tool 10 between the nozzle opening 22 and the attachment end 24. The elongated portion 12 is preferably slightly tapered, so that the air flow channel increases in area from the nozzle opening 22 to the attachment end 24. The narrowing of the air flow channel 30 near the nozzle opening 22 increases suction at the nozzle opening 22.

The elongated portion 12 can further be formed with a plurality of circumferential furrows 32. As illustrated, the furrows 32 can be formed in the exterior surface 17 of the elongated portion 12. Preferably, the furrows are formed on substantially the entire length of the elongated portion 12. The furrows 32 are spaced from one another by a distance S, and preferably, the distance S is roughly equal between each furrow 32. The furrows 32 have a width W, which is relatively narrow in comparison with the distance S. The furrows 32 are formed transverse to the longitudinal axis X of the crevice tool 10, and can lie in an series of planes $P_F$ that are parallel to the plane $P_N$ of the nozzle rim 21. It is further noted that that the planes $P_F$ and $P_N$ lie at an acute angle to the normal axis N. This configuration imparts the greatest amount of flexibility of the elongated portion 12 while holding the crevice tool 10 in an ergonomic manner.

Figure 5:
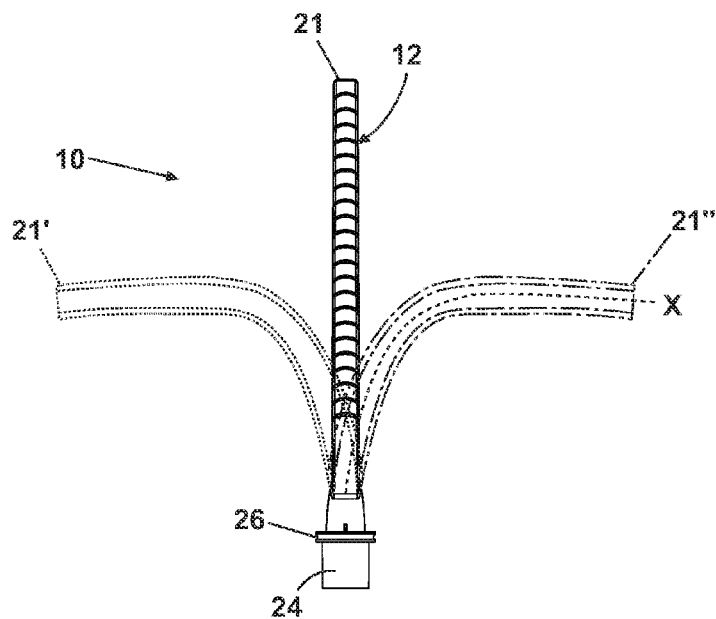
FIG. 5 is a top view of the flexible crevice tool from FIG. 1, illustrating the side-to-side flexing of the crevice tool.
Figure 6:
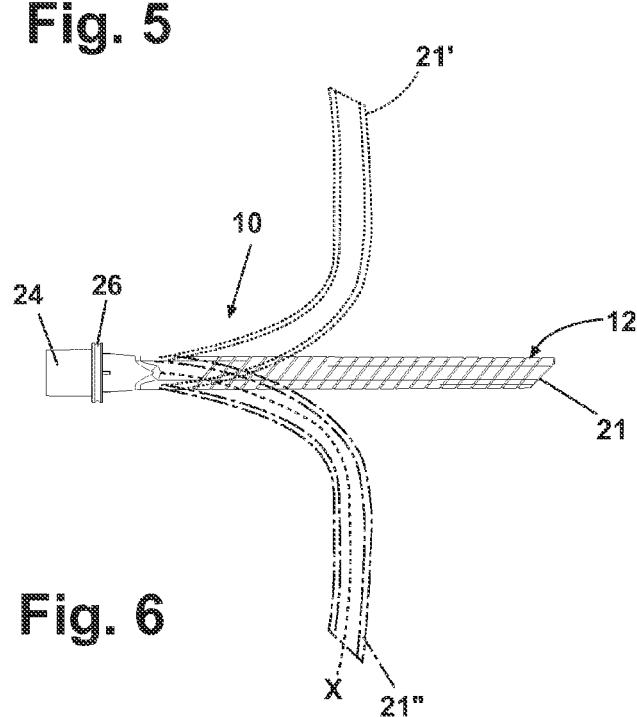
FIG. 6 is a side view of the flexible crevice tool from FIG. 1, illustrating the up-and-down flexing of the crevice tool.

The furrows 32 function to increase the flexing of the crevice tool 10 as illustrated by FIGS. 5 and 6, whereby the elongated portion 12 of the crevice tool 10 can be flexed in multiple directions as indicated by the phantom line drawings of the crevice tool 10. As shown in FIG. 5, the elongated portion 12 of the crevice tool 10 can be flexed laterally (side-to-side) such that the longitudinal axis X of the crevice tool 10 at the nozzle opening 22 is orientated at a bend angle up to 90° to the longitudinal axis X at the attachment end 24, without kinking or breaking of the elongated portion 12. As shown in FIG. 6, the elongated portion 12 of the crevice tool 10 can be flexed longitudinally (up and down) such that the longitudinal axis X of the crevice tool 10 at the nozzle opening 22 is orientated at a bend angle up to 90° to the longitudinal axis X at the attachment end 24, without kinking or breaking of the elongated portion 12. As illustrated, the bend angle of the crevice tool 10 is substantially equal whether flexing the elongated portion 12 laterally or longitudinally. The elongated portion 12 of the crevice tool 10 can further be flexed in a combination of lateral and longitudinal flexing. Moreover, since the furrows 32 are formed on substantially the entire length of the elongated portion 12, the elongated portion 12 can flex along substantially its entire length.

The crevice tool 10 can optionally comprise a wire (not shown) affixed to or molded within the elongated portion 12. The wire is sufficiently flexible or malleable so that the elongated portion 12 can be formed to and can remain in a desire arc without having to apply flexing pressure to the crevice tool 10.

While the invention has been specifically described in connection with certain specific embodiments thereof, it is to be understood that the description is by way of illustration of one embodiment of the invention and not of limitation. Reasonable variation and modification are possible within the forgoing description and drawings without departing from the scope of the invention which is defined in the appended claims.

What is claimed is:

1. An accessory tool for a vacuum cleaner comprising:
   a body having an attachment end for attachment to a suction hose and an elongated portion having an exterior surface, a substantially smooth interior surface defining an air flow channel, and a nozzle opening in fluid communication with the air flow channel for ingestion of debris-containing air; and
   a plurality of spaced furrows formed in the exterior surface transverse to a longitudinal axis of the body, the furrows having a relatively narrow width as compared with the spacing on each side of the furrows;
   wherein the elongated portion has two spaced, straight side walls joined by a curved upper wall and a curved lower wall which together define a cross-sectional configuration perpendicular to the longitudinal axis;
   wherein the furrows are shaped and the elongated portion is made of a material that is selected to impart flexibility to the elongated portion transversely to the longitudinal axis;
   wherein the nozzle opening comprises a rim that lies in a plane at an acute angle to the longitudinal axis of the body; and
   where the furrows lie in planes that are parallel to the plane of the rim.

2. The accessory tool of claim 1, wherein the furrows are circumferentially formed in the exterior surface around the elongated portion.

3. The accessory tool of claim 1, wherein the body is integrally molded in one piece.

4. The accessory tool of claim 1, wherein the elongated portion is oval in cross-sectional configuration.

5. The accessory tool of claim 1, wherein the elongated portion tapers toward the nozzle opening.

6. The accessory tool of claim 1, wherein at least the elongated portion is made of one of nitrile rubber, thermoplastic urethane, polypropylene, and polyurethane.

7. The accessory tool of claim 1, wherein the furrows are shaped and the elongated portion is made of a material so that the longitudinal axis of the elongated portion is bendable about a radius through an angle of at least 45° without kinking or breaking.

8. The accessory tool of claim 1 wherein the furrows are shaped and the elongated portion is made of a material so that the longitudinal axis of the elongated portion can be bent about a radius through an angle of at least 90° without kinking or breaking.

9. An accessory tool for a vacuum cleaner comprising:
a body having an attachment end for attachment to a suction hose and an elongated portion having an exterior surface, a substantially smooth interior surface defining an air flow channel, and a nozzle opening in fluid communication with the air flow channel for ingestion of debris-containing air;
a plurality of spaced furrows formed in the exterior surface transverse to a longitudinal axis of the body, the furrows having a relatively narrow width as compared with the spacing on each side of the furrows; and
a wire affixed to or within the elongated portion, wherein the wire has sufficiently stiffness and malleability so that the elongated portion can be formed to and can releasably remain in bent position;
wherein the elongated portion has two spaced, straight side walls joined by a curved upper wall and a curved lower wall which together define a cross-sectional configurations perpendicular to the longitudinal axis; and
wherein the furrows are shaped and the elongated portion is made of a material that is selected to impart flexibility to the elongated portion transversely to the longitudinal axis.

10. An accessory tool for a vacuum cleaner comprising:
a body having an attachment end for attachment to a suction hose and an elongated portion having an exterior surface, a substantially smooth interior surface, two spaced, straight side walls joined by a curved upper wall and a curved lower wall which together define a cross-sectional configuration perpendicular to a longitudinal axis, and a nozzle opening for ingestion of debris-containing air;
a wire affixed to or within the elongated portion, wherein the wire has sufficiently stiffness and malleability so that the elongated portion can be formed to and can releasably remain in bent position; and
a plurality of spaced furrows formed in an exterior surface of the body, the furrows having a relatively narrow width as compared with the spacing on each side of the furrows;
wherein the furrows are shaped and the elongated portion is made of a material to impart flexibility to the elongated portion transversely to the longitudinal axis so that the longitudinal axis of the elongated portion can be bent about a radius through an angle of at least 45° without kinking or breaking.

11. The accessory tool of claim 10 wherein the furrows are shaped and the elongated portion is made of a material so that the longitudinal axis of the elongated portion can be bent about a radius through an angle of at least 90° without kinking or breaking.

12. The accessory tool of claim 11 wherein the elongated portion is oval in cross-sectional configuration.

13. The accessory tool of claim 12 wherein the elongated portion tapers toward the nozzle opening.

14. The accessory tool of claim 10 wherein at least the elongated portion is made of one of nitrile rubber, thermoplastic urethane, polypropylene, and polyurethane.

15. The accessory tool of claim 10 wherein the furrows are shaped and the elongated portion is made of a material so that the longitudinal axis of the elongated portion can be bent about a radius through an angle of at least 45° without kinking or breaking in a direction transverse to and laterally of elongated cross-sectional configuration.

16. A crevice tool for a vacuum cleaner comprising:
an attachment end for attachment to a suction hose, the attachment end having an opening that extends along a normal axis of the tool;
an elongated portion extending from the attachment end and defining a longitudinal axis of the tool, the elongated portion having two spaced, straight side walls joined by a curved upper wall and a curved lower wall which together define a cross-sectional configuration parallel to the normal axis, and comprising:
an exterior surface;
a substantially smooth interior surface defining an air flow channel; and
a nozzle opening in fluid communication with the air flow channel for ingestion of debris-containing air, wherein the nozzle opening lies in a plane at an acute angle to the longitudinal axis and the normal axis; and
a plurality of spaced furrows formed in the exterior surface transverse to the longitudinal axis, the furrows having a relatively narrow width as compared with the spacing on each side of the furrows;
wherein the furrows lie in planes that are parallel to the plane of the nozzle opening, and the furrows impart flexibility to the elongated portion transversely to the longitudinal axis.

17. The crevice tool of claim 16, wherein the attachment end comprises a substantially circular cross-section parallel to the normal axis for attachment to a suction hose.

* * * * *